United States Patent [19]

Rubin

[11] Patent Number: 4,908,162

[45] Date of Patent: Mar. 13, 1990

[54] METHOD OF MAKING TRIPLE BONDED UNSATURATED FATTY ACIDS

[76] Inventor: David Rubin, 8949 Montrose Way, San Diego, Calif. 92122

[21] Appl. No.: 310,205

[22] Filed: Feb. 14, 1989

Related U.S. Application Data

[63] Continuation-in-part of Ser. No. 276,467, Nov. 22, 1988.

[51] Int. Cl.$^4$ .............................................. C09F 5/00
[52] U.S. Cl. ............................ 260/405.5; 260/410.5; 585/538; 514/169
[58] Field of Search ........................ 260/410.5, 405.5; 585/538

[56] References Cited

U.S. PATENT DOCUMENTS

| | | | |
|---|---|---|---|
| 3,799,997 | 3/1974 | Schmerling | 260/654 |
| 4,181,670 | 1/1980 | Liang | 260/410.5 |
| 4,181,725 | 1/1980 | Voorhes et al. | 424/258 |
| 4,190,669 | 2/1980 | Voorhes et al. | 424/305 |
| 4,345,084 | 8/1982 | Chan et al. | 548/237 |
| 4,584,320 | 4/1986 | Rubin | 514/560 |
| 4,616,002 | 10/1986 | Kauber et al. | 514/18 |
| 4,837,348 | 6/1989 | Stolowitz et al. | 556/9 |

FOREIGN PATENT DOCUMENTS

| | | | |
|---|---|---|---|
| 2584400 | 7/1985 | European Pat. Off. | |
| 0010198 | 2/1981 | Japan | 558/170 |
| 0013593 | 1/1983 | Japan | 558/170 |

OTHER PUBLICATIONS

CA 90:103380m, Metcalf and Jung, "Acetylenic Amines Useful as Inhibitors of Decarboxylases".
CA 87:44143z, Welters, Gehlhaus and Gernot "Light-Protective Agent for Cosmetic Use".
*Prostglandins* 29 (3): 431-441, 1985.
*Prostglandins* 26 (6): 1011-1020, 1983.
*Prostaglandins* 21 (2): 323-332, 1981.
*Prostaglandins* 21 (2): 333-343, 1981.
*Prostaglandins* 12 (2): 187-192, 1976.
*J. Biol. Chem.* 255 (7): 8023-8026, 1980.
Haviv et al., *J. Med. Chem.* 30: 254-263, 1987.
Parish, Jr., et al., *Lipids,* 18 (12): 894-895, 1983.
Voorhes, *Arch. Dermatol.* 119: 541-547, 1983.
Humes et al., *Biochemical Pharmacology* 32 (15): 2319-2322, 1983.
Verrando et al., *British Journal of Dermatology* 109, Supplement 25: 120-123, 1983.
Salari et al., *Prostaglandins, Leukotrienes, and Medicine* 13: 53-60, 1984.
Chemical Abstracts 88: 151990r.
Chemical Abstracts 97: 38706a.
Chemical Abstracts 105: 226110j.
Chemical Abstracts, 107: 129709v.
Orning et al., *J. Biol. Chem.* 255 (7): 8023-8026, 1980.
Evans et al., *Chemistry and Physics of Lipids* 38: 327-342, 1985.
Kunan et al., Hoppe-Seyler's *Z. Physiol. Chem.* 352, pp. 542-548, 1971.

*Primary Examiner*—Mukund J. Shah
*Assistant Examiner*—Celia Chang
*Attorney, Agent, or Firm*—Browdy and Neimark

[57] ABSTRACT

A method is provided for preparing unsaturated fatty acids having triple bonds by reducing the double bonds of unsaturated fatty acids. The unsaturated, double-bonded fatty acid is reacted with a halogen gas to form a halogenated fatty acid, and this brominated fattay acid is mixed with a strong base and 1,3-dicyclohexylcarbodiimide to form a salt of a triple bonded fatty acid. This salt is then reacted with an acid to form the desired triple bonded fatty acid.

11 Claims, No Drawings

METHOD OF MAKING TRIPLE BONDED UNSATURATED FATTY ACIDS

The present invention is a continuation-in-part of application Ser. No. 07/276,467, filed Nov. 22, 1988, the entire contents of which are hereby incorporated by reference.

FIELD OF THE INVENTION

The present invention relates to methods for preparing unsaturated fatty acids having triple bonds.

BACKGROUND OF THE INVENTION

The alternate designations for fatty acids used throughout the present specification, such as C20:4ω6, refer to the total number of carbon atoms in the chain before the colon; the number of unsaturated bonds after the colon; and the number of carbon atoms from the end opposite the carboxylic acid at which the first unsaturation appears, following the omega ω. Members of a given omega series of fatty acids, e.g., ω-3, can usually be converted to acids of differing lengths and total number of unsaturations by normal body enzymes, but it is generally impossible to change a compound from one omega series to another, e.g., ω-3 to ω-6. This is because the enzymes generally cause changes of length and unsaturation to occur starting from the carboxylic acid end of the chain.

Arachidonic acid is stored in the membranes of the body as part of the phospholipids. The arachidonic acid is released from the phospholipids by the action of a phospholipase. The production of the phospholipase, which causes release of arachidonic acid, may be triggered by any one of a variety of mechanisms, including physical irritation and hypersensitivity. Once the arachidonic acid is released into the circulation, it may be oxidized by two different pathways. It is either metabolized by cyclo-oxygenase to produce prostaglandins, or by lipoxygenase to generate hydroperoxy derivatives which may be further metabolized to leucotrienes and SRS-A.

It has previously been theorized that SRS-A production can be inhibited by the inhibition of one or more of the enzymes required for its formation. For example, it is known that corticosteroids act to inhibit the phospholipase stage. Thus, the release of arachidonic acid is inhibited, causing the inhibition of the production of all of the metabolites of arachidonic acid, including the prostaglandins. Because of this, corticosteroids have been used as anti-inflammatories (for inhibition of prostaglandins) as well as anti-asthmatics (inhibition of SRS-A). Unfortunately, however, corticosteroids have severe and undesirable side effects.

Aspirin-like compounds and indomethacin inhibit only the cyclo-oxygenase pathway of arachidonic acid metabolism. Thus, these compounds can do nothing toward the treatment of asthmatic conditions and, in fact, giving aspirin to an asthmatic may provoke an attack because the aspirin forces SRS-A production by inhibiting the cyclo-oxygenase pathway of arachidonic acid.

Compounds which inhibit both the cyclo-oxygenase and lipoxygenase pathways for arachidonic acid metabolism can be expected to reduce SRS-A formation, but are also expected to have undesirable side effects due to the inhibition of the cyclo-oxygenase pathway, as, for example, the formation of stomach ulcers. Furthermore, substantially non-toxic natural substances which inhibit both cyclo-oxygenase and lipoxygenase are not known.

Another reason it is undesirable for an anti-asthmatic drug to inhibit cyclo-oxygenase is because cyclo-oxygenase is involved in the metabolism of PGE from dihomo-gamma-linolenic acid (C20:6ω6), which is an important and desirable prostaglandin. PGE1 interferes with the biosynthesis of cholesterol and endothelial cell proliferation.

There are a variety of lipoxygenases which oxidize various points of the arachidonic acid molecule. The lipoxygenase which catalyzes the production of SRS-A is the 5-lipoxygenase, which oxidizes the double bond of the 5-carbon atom or arachidonic acid. It is thus desirable specifically to inhibit 5-lipoxygenase, thus avoiding inhibition of other enzymes which produce products which are not necessarily undesirable.

The best drug for reduction of SRS-A and thereby for treatment of asthmatic attacks and bronchial spasms would be a specific 5-lipoxygenase inhibitor which does not inhibit cyclo-oxygenase or other lipoxygenases. Preferably, such a compound should be as nontoxic as possible.

Highly unsaturated fatty acids have been found to be particularly concentrated when there is a requirement for rapid movement at a cellular level such as may be required in transport mechanisms, for example, in the brain and its synaptic junctions, and the retina, where only the long-chain derivatives of the essential fatty acids are found, and not the parent linoleic and α-linolenic acids. The linoleic series can produce a docosapentaenoic acid (C20:4ω6), but the main component used in cell membranes is arachidonic acid. In the α-linolenic series the main metabolite is docosaenoic acid. These long-chain derivatives are the principal components of cell structural lipids and also include the direct precursors for prostaglandins and leukotrienes.

The enzyme systems for the metabolism of fatty acids are, in general, shared. This means that the different fatty acids will compete with each other. It is known, for example, that saturated fats suppress the activity of essential fatty acid. If a part of the prostaglandin system is directly related to diet via metabolism of linoleic acid or can be controlled by using competing fatty acids such as eicosapentaenoic acid, it may be possible to take advantage of the competition that exists between the fatty acids for adjusting the desaturase, cyclo-oxygenase, or lipoxygenase enzyme systems.

Rubin, in U.S. Patent No. 4,584,320, discloses a composition for treating conditions caused by excessive release of SRS-A, consisting essentially of an amount effective to inhibit release of SRS-A of 8,11,14,17-eicosatetraenoic acid or a pharmaceutically acceptable salt or ester thereof in a pharmaceutically acceptable vehicle, and a method for the treatment of conditions caused by excessive release of SRS-A, comprising administering to a patient having such condition an amount of 8,11,14,17-eicosatetraenoic acid or a pharmaceutically acceptable salt or ester thereof effective to inhibit the release of SRS-A.

This compound is similar in structure to arachidonic acid but is not metabolized by the enzyme 5-lipoxygenase in SRS-A. This compound is thus a competitive inhibitor, reacting with 5-lipoxygenase instead of arachidonic acid, and thus preventing the production of SRS-A.

Evans et al., in *Prostaglandins* 29 (3): 431–441, 1985, disclose that eicosa-5,8,11,14-tetraynoic acid is known to strongly inhibit both 12-lipoxygenase and cyclooxygenase. Additionally, eicosa-4,7,10,13-tetraynoic and henicos-5,8,11,14-tetraynoic acids were found to inhibit platelet lipoxygenase but not cyclooxygenase. Additionally, eicosa-5,8,14-triynoic acid and eicosa-5,11,14-triynoic acids were found to inhibit cyclooxygenase but were inactive against lipoxygenase.

Reich et al., in *Prostaolandins* 26 (6): 1011–1020, 1983, disclose that 5,8,11-eicosatriynoic acid' reduced the number of ova released from treated ovaries in a dose-dependent manner.

Wilhelm et al., in *Prostaglandins* 21 (2): 323–332, 1981, report that, of nine acetylenic acids examined, both 4,7,10,13-eicosatetraynoic acid and 5,8,11-14-henicosatetraynoic acid inhibit lipoxygenase more than 95 percent without any significant reduction in thromboxane B2 or HHT synthesis.

Sun et al., in *Prostaolandins* 21 (2): 333–343, 1981, disclose the inhibition of platelet arachidonic acid 12-lipoxygenase by acetylenic acid compounds including 4,7,10,13-eicosatetraynoic acid; 5,8,11,14eicosatetraynoic acid. L Goetz et al., in *Prostaolandins* 12 (2): 187–192, 1976, discloses that acetylenic acids inhibit prostaglandin synthesis from eicosa-8,11,14-trienoic acid in microsomes. Octadeca-6,9,12- triynoic acid and eicosa-8,11,14-triynoic acid were found to be the most potent inhibitors, the presence of an ω-8 methylene group being their commonality, although the presence of an ω-8 methylene group is not the only determinant of inhibitory potency.

Voorhees et al., in U.S. Patents 4,181,725 and 4,190,669, disclose that eicosa-5,8,11,14-tetraynoic acid or 5,8,11-eicosatriynoic acid can be used to treat psoriasis. In French patent 2 584 400, it is disclosed that esters and amides of eicosatriynoic acid can be used to treat inflammatory skin conditions such as psoriasis, eczema, acne, and the like.

Orning et al., in *J. Biol. Chem.* 255 (7): 8023–8026, 1980; disclose that 5,8,11-eicosatriynoic acid is a known lipoxygenase inhibitor, prevents the biosynthesis of leukotriene C4 by mastocytoma cells.

Evans et al., in *Chemistry and Physics of Lipids* 38: 327–342, 1985, disclose a method for synthesizing 5,8,14-icosatrienoic acid and 5, 11,14-icosatrienoic acid and their acetylenic analogues by hydrogen abstraction from a methylene carbon atom located at the center of a 1,4-ci pentadiene system.

Kunau et al., in Hoppe-Seyler's Z. *Physiol. Chem.* 352, pp 542–548, 1971, disclose a method for synthesizing polyynoic acids having four, five, and six triple bonds from alcohols already having triple bonds.

A number of ω-3 fatty acids having triple bonds at the 5-, 8-, and/or 11-position have been found to be useful in treating asthma, as disclosed in copending application Serial No. 07/276,467, Nov. 22, 1988, and incorporated herein by reference.

SUMMARY OF THE INVENTION

It is an object of the present invention to provide a simplified method for preparing fatty acids having triple bonds.

It is another object of the present invention to provide a method for preparing compounds which can be administered to prevent asthmatic attacks.

According to the present invention, fatty acids can be reduced according to the following reaction to provide triple bonded acids:

The present method provides a simple method for reducing the double bonds of the fatty acids, which is superior to the known methods for making these compounds.

The triple bonded fatty acids of the present invention form a "false metabolite", competing with arachidonic acid on the 5-lipoxygenase enzyme. Since the triple bond in the fatty acids of the present invention occupies a smaller space than the double bonds on arachidonic acid, the triple bonded fatty acid penetrates more firmly to the active site of the 5-lipoxygenase enzyme and simultaneously creates hydrogen bonds with the enzyme molecule itself. These bonds are more stable than those formed with the double bonded acids, and thus, once the substrate-enzyme complex is formed, a stable complex is formed which does not readily decompose. This reaction effectively denatures the enzyme, and prevents it from continuing to catalyze the peroxidation reaction. Because the triple bonded acids of the present invention are not competitive inhibitors which compete as a substrate with arachidonic acid for the 5-lipoxygenase enzyme, the inhibition of the triple bonded acids is orders of magnitude greater than for mere inhibitors of the arachidonic acid oxidation reaction.

The process of the present invention comprises treating double bonded fatty acids with a halogen to halogenate the acid. The halogenated acid is then mixed with a dry, concentrated ethanolic solution of a base to form a salt. The salt is then washed with an acid to yield a triple bonded free fatty acid.

This process of the present invention can be applied to any fatty acid having double bonds to form the corresponding fatty acid having the desired number of triple bonds rather than double bonds. The term "fatty acid" herein refers to acid having from about eight to about thirty carbon atoms in the chain. Of particular interest are the ω-3 fatty acids, although the process of the present invention can be used to oxidize the double bonds of any type of fatty acid having at least two double bonds.

The fatty acids which are particularly well suited to the process of the present invention are those fatty acids which have double bonds at the 5-position, and optionally at the 8-, 11- and 14-positions as well. During the reduction according to the present invention, all of the double bonds of the acid can be reduced, without the formation of undesirable side products.

DETAILED DESCRIPTION OF THE INVENTION

Triple bonded fatty acids are prepared according to the present invention by introducing a halogen, such as chlorine, bromine, or iodine, into a dry solution of the acid to be reduced. Ethanol is a convenient solvent for this process, although any polar organic solvent that can be conveniently dried, such as methanol, acetone, or the like, can be used. The halogenated fatty acid is then mixed with a dry concentrated solution of a base such as potassium or sodium hydroxide in a suitable anhydrous solvent, such as ethanol. This reaction is catalyzed by Dcc, 1,3-dicyclohexylcarbodiimide (N,N'-dicyclohexylcarbodiimide, dicyclodexylcarbodiimide). The salt is then washed with an acid such as acetic acid to yield a 20-carbon free fatty acid with five triple bonds. Any acid can be used for this purpose, although sulfuric, acetic, and hydrochloric are among the most convenient.

EXAMPLE I 1 mole of eicosapentaenoic acid having double bonds at the 5-, 8-, 11-, 14-, and 17-positions was dissolved in anhydrous ethanol, and 5 moles of bromine gas was bubbled through the mixture. The mixture was then mixed with a dry ethanolic solution of potassium hydroxide for a total of 10 moles of potassium hydroxide and 1 gram of Dcc. The resulting potassium salt was then washed with a total of 200 cc. 5% acetic acid to form the free fatty acid having triple bonds. The reaction scheme is as follows:

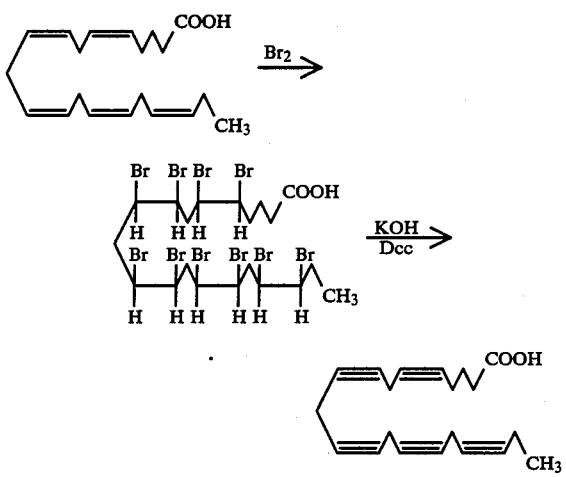

EXAMPLE II

As described above, a 22-carbon fatty acid having six double bonds is reacted with bromine gas in anhydrous ethanol, and is then contacted with a concentrated ethanolic solution of sodium hydroxide in the presence of Dcc. The resulting sodium salt is washed with acetic acid to yield a 22-carbon fatty acid having six triple bonds.

EXAMPLE III

A 16-carbon fatty acid having four double bonds is reacted with iodine gas in anhydrous methanolic solution, and is then mixed with a dry concentrated solution of potassium hydroxide in methanol in the presence of Dcc. The resulting sodium salt is washed with acetic acid to yield a free fatty acid having 16 carbon atoms and four triple bonds.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. A method for preparing an unsaturated fatty acid having triple bonds comprising;
   reacting an unsaturated fatty acid having double bonds with a halogen to form a halogenated fatty acid;
   mixing said halogenated fatty acid with a strong base and dicyclohexylcarbodiimide to form a salt of a triple bonded fatty acid; and
   reacting said salt with an acid to form a triple bonded unsaturated fatty acid.
2. The method of claim 1 wherein the unsaturated fatty acid is an $\omega$-3 fatty acid.
3. The method of claim 2 wherein the fatty acid is selected from the group consisting of fatty acids having from about 8 to about 30 carbon atoms.
4. The method of claim 1 wherein the fatty acid has from three to seven double bonds.
5. The method of claim 1 wherein the strong base is selected from the group consisting of sodium hydroxide and potassium hydroxide.
6. The method of claim 1 wherein the reaction is conducted in anhydrous alcoholic solution.
7. The method of claim 4 wherein the double bonds in the fatty acid are located at positions selected from the group consisting of the 5-, 8-, 11-, 14-, and 17-positions.
8. The method of claim 7 wherein the fatty acid is eicosapentaenoic acid.
9. The method of claim 1 wherein the halogen is bromine.
10. The method of claim 1 wherein the halogen is chlorine.
11. The method of claim 1 wherein the acid is acetic acid.

* * * * *